United States Patent [19]

Peterson et al.

[11] Patent Number: 5,141,767
[45] Date of Patent: Aug. 25, 1992

[54] METHOD FOR PROVIDING A MEASURE OF TACKINESS OF A BODY SURFACE

[75] Inventors: John P. Peterson, Chapel Hill; David E. Graves; Alan L. Crowle, both of Raleigh, all of N.C.

[73] Assignee: Northern Telecom Limited, Montreal, Canada

[21] Appl. No.: 641,307

[22] Filed: Jan. 15, 1991

[51] Int. Cl.$^5$ .............................. G01N 19/00
[52] U.S. Cl. ........................ 427/8; 73/150 R
[58] Field of Search ............ 427/8, 96, 180; 73/150 R; 118/309

[56] References Cited

U.S. PATENT DOCUMENTS

| | | | |
|---|---|---|---|
| 2,602,417 | 7/1952 | Medcalf | 118/309 |
| 3,012,900 | 12/1961 | Kleinmann et al. | 427/212 |
| 3,603,287 | 9/1971 | Christy et al. | 118/309 |
| 3,799,112 | 3/1974 | Huteaux | 118/629 |
| 3,870,016 | 3/1975 | Schneider | 118/309 |
| 4,294,111 | 10/1981 | Rutledge et al. | 75/150 R |
| 4,954,409 | 9/1990 | Aoki et al. | 430/108 |
| 5,056,460 | 10/1991 | Vöhringer | 118/634 |

*Primary Examiner*—Shrive Beck
*Assistant Examiner*—Terry J. Owens
*Attorney, Agent, or Firm*—Shlesinger, Arkwright & Garvey

[57] ABSTRACT

An apparatus, for determining the degree of tackiness of a surface of a body, comprises a closed chamber with inlet and outlet openings; a support for the body within the chamber; a fan for providing an airflow directed toward the surface of the body within the chamber; a powder dispenser for releasing powder into the path of the airflow upstream of the body surface, the powder being adapted to be carried by the airflow thereby to permit the powder to impinge against the body surface; whereby the amount of powder adhering to the body surface after a period provides a measure of tackiness of the surface.

8 Claims, 2 Drawing Sheets

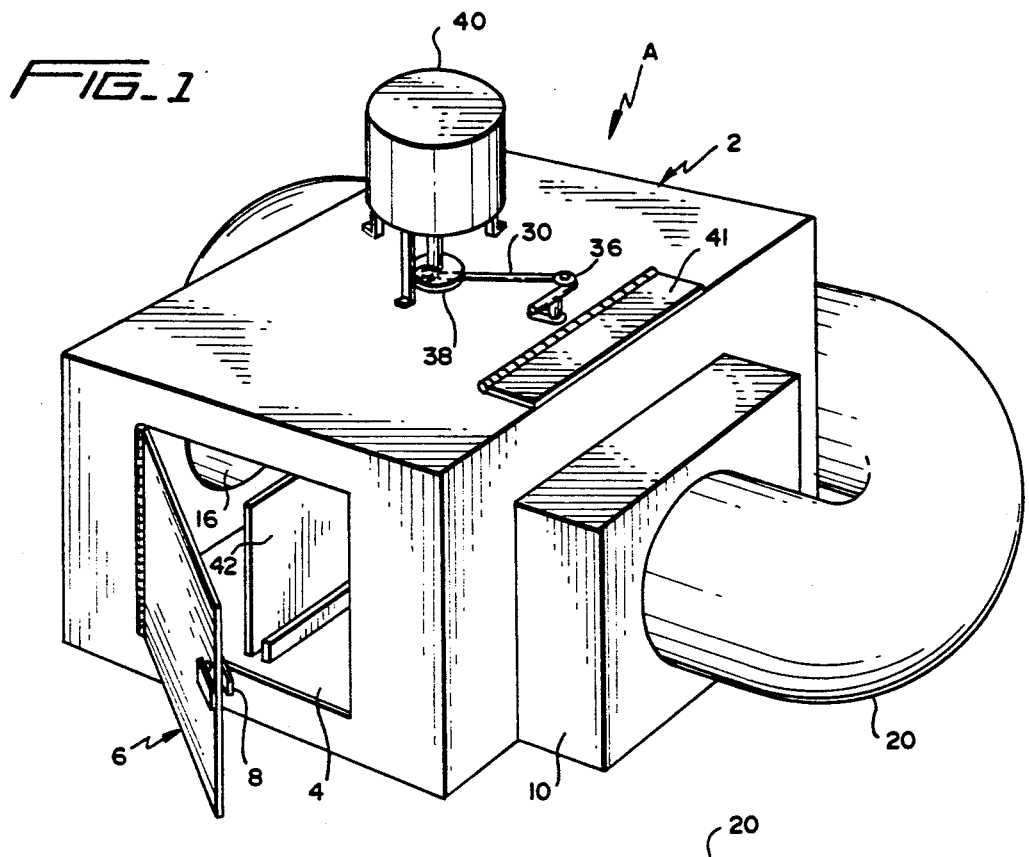
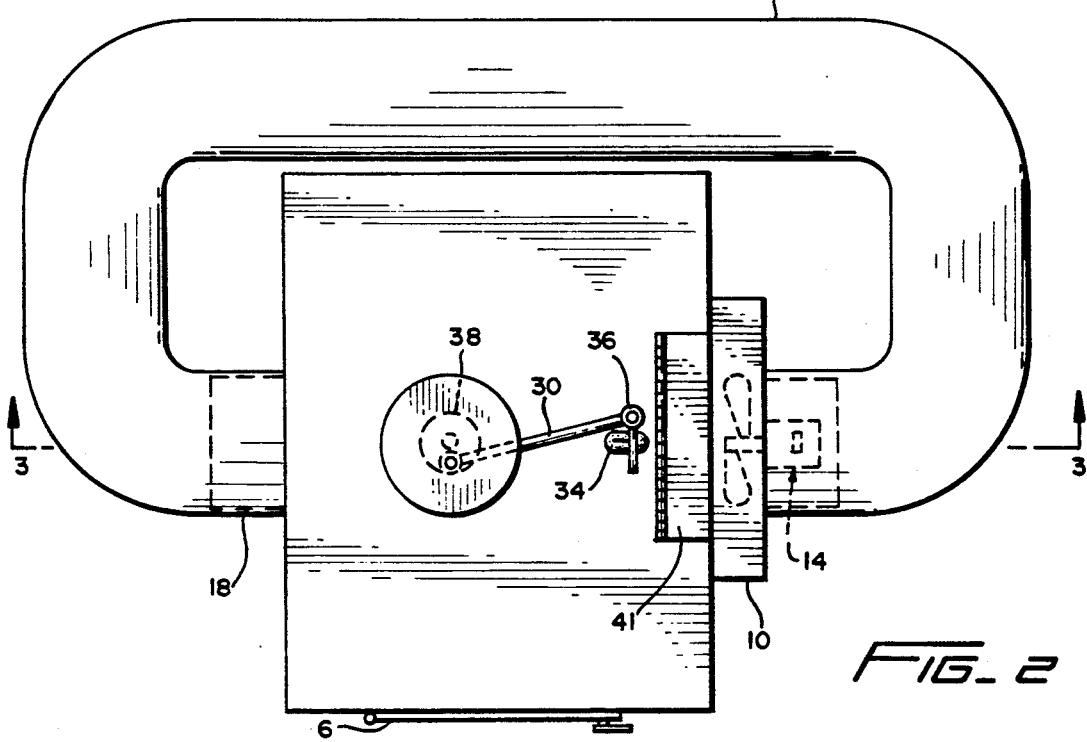

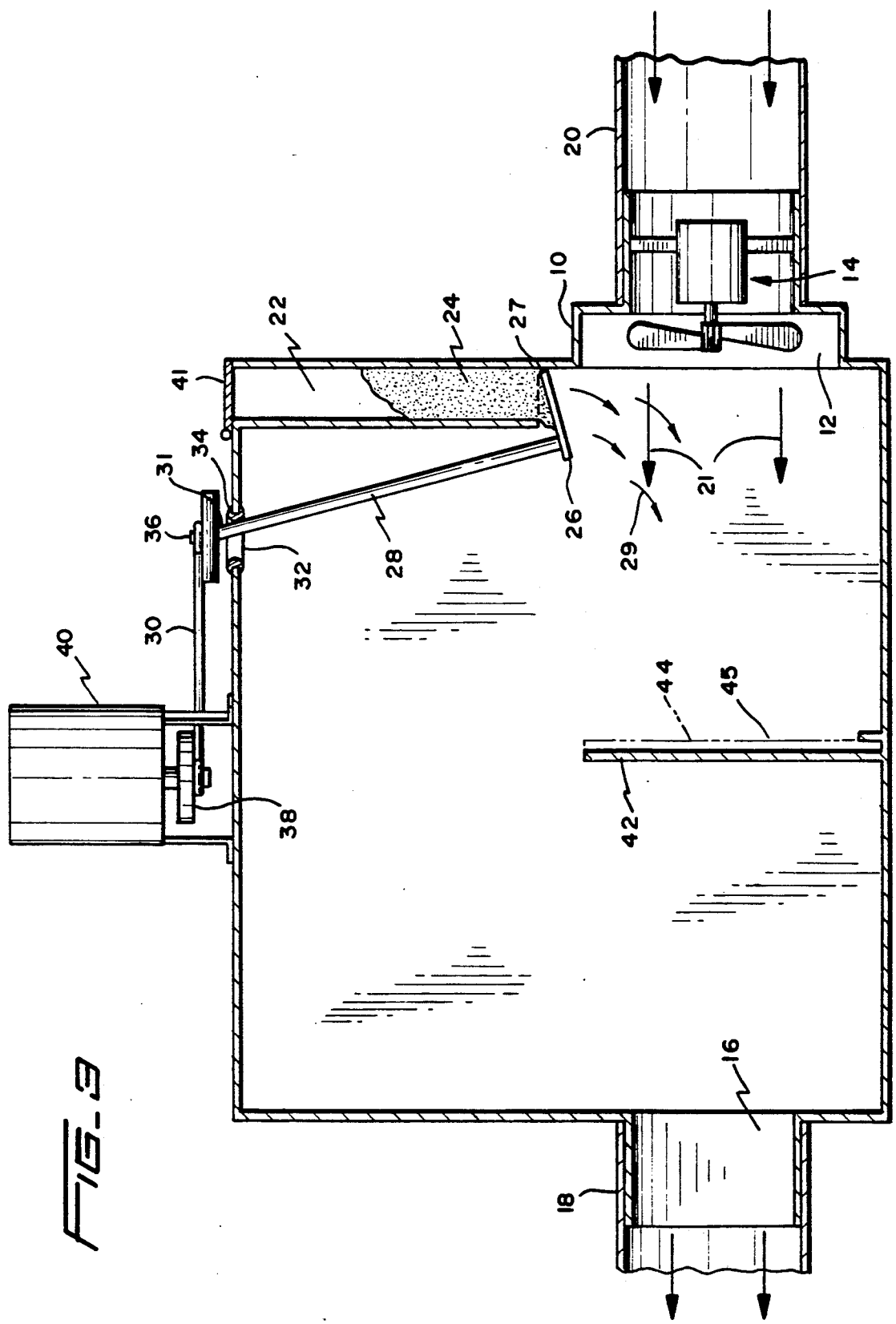

METHOD FOR PROVIDING A MEASURE OF TACKINESS OF A BODY SURFACE

FIELD OF THE INVENTION

The present invention relates generally to an apparatus for providing a measure of degree of tackiness of a surface and particularly to a tackiness tester employing a dusting chamber.

BACKGROUND OF THE INVENTION

A circuit board, before circuit components are connected onto it, is typically coated with flux, which aids in the soldering of the circuit components onto the board. After the components are soldered, the circuit board is typically washed with fluid containing CFC (Chlorinatedfluorocarbon), such as FREON, to remove any excess flux. Because CFC is known to be harmful to the environment, it is desired that the use of CFC be eliminated, while maintaining the reliability and quality of the circuit board.

The use of CFC may be eliminated if low solids flux is used and the amount that is deposited on the circuit board is carefully controlled such that only the required amount necessary for the soldering process is deposited on the circuit board. To maintain quality control, it is necessary to have a means for objectively monitoring the consistency of the flux deposit process. One such means is an apparatus, in accordance with the present invention, for measuring the degree of tackiness of the flux coated circuit board.

OBJECTS AND SUMMARY OF THE INVENTION

It is therefore an Object of the present invention to provide an apparatus for monitoring the proper amount of flux deposited on a circuit board such that excess flux is substantially eliminated, thereby eliminating washing with CFC fluid.

It is another object of the present invention to provide a tackiness tester that provides a consistent means for determining the degree of tackiness of a flux coated circuit board.

It is still another object of the present invention to provide a tackiness tester that provides a standardized means for gauging the relative amount of deposited flux between a number of circuit boards.

It is yet another object of the present invention to provide a tackiness tester that is relatively simple and inexpensive to manufacture.

In summary, the present invention provides a tackiness tester that is designed to eliminate the use of CFC in circuit board assembly by providing a means for monitoring the amount of flux deposited on the circuit board such that only the amount needed is used and any excess amount is avoided.

These and other objects of the present invention will become apparent from the following detailed description.

BRIEF DESCRIPTIONS OF THE DRAWINGS

FIG. 1 is a perspective schematic view of a tackiness tester according to the present invention.

FIG. 2 is a top view of the tackiness tester shown in FIG. 1, with portions shown in phantom lines.

FIG. 3 is a cross-sectional view taken along line 3—3 in FIG. 2.

DETAILED DESCRIPTION OF THE INVENTION

An embodiment of a tackiness tester A according to the present invention comprises a closed chamber 2 with an opening 4 and a hingedly operable door 6 for access into the chamber 2, as best shown in FIG. 1. A lock 8 permits the door 6 to be in the closed position during operation.

A fan housing 10 is operably associated with one side of the chamber 2 and communicates with an inlet opening 12 into the interior of the chamber 2. An electric fan 14 is operably secured within the housing 10. An outlet opening 16, defined by a collar 18, is disposed on an opposite side of the chamber 2 relative to the inlet opening 12. A duct 20 connects the outlet opening 16 with the inlet opening 12 and advantageously provides a return path for the airflow 21 when the fan 14 is operating, as best shown in FIG. 3.

A storage bin 22 for powder 24 is disposed adjacent and above the fan 14, as best shown in FIG. 3. The bin 22 has a hingedly mounted bottom door 26, which is operated such that it is alternately moved about its hinge line 27 to discharge the powder 24, as generally indicated at 29, into the airflow 21 generated by the fan 14, as best shown in FIG. 3.

A rod 28 is loosely connected at its one end to the door 26 and at its other end to a connecting rod 30. A portion 31 of the rod 28 protrudes outside the chamber 2 through a slot 32 which remains closed by means of a flexible cover 34. The rod 30 is pivotally connected to the rod 28 at pivot 36. The other end of the rod 30 is pivotally connected to a crank 38 that is driven by an electric motor 40.

Movement of the rod 28 during operation causes the release of the powder 24 into the airflow 21. A person of ordinary skill in the art will understand that there are other means for causing the powder 24 to be released to the airflow 21.

The bin 22 is provided with a hingedly operated cover 41 at its top portion for reloading with the powder 24.

A support 42, disposed within the chamber 2 substantially transverse to the airflow 21, provides supporting means for a test board 44 (shown in dashed lines) such that its surface 45 is preferably oriented vertically and exposed directly to the airflow 21. A person of ordinary skill in the art will understand that there are other means for supporting the test board 44 within the chamber 2.

OPERATION

In operation, the test board 44 to be tested for tackiness with its surface 45 coated with flux is positioned within the chamber 2 and secured in the support 42. The board 44 is preferably positioned such that the surface 45 is oriented vertically, as best shown in FIG. 3. The vertical orientation of the surface 45 advantageously permits any excess powder to drop to the bottom of the chamber 2. The test board is disposed within the chamber 2 such that the surface 45 will be in the direct path of the airflow 21.

The fan 14 is then energized, generating the airflow 21, which follows a path from the inlet 12 to the outlet 16. A person of ordinary skill in the art will understand that there are other means of generating the airflow 21, such as compressed air, etc.

The motor 40 is next turned on. The crank 38, which is operably connected to the motor 40, rotates and causes the connecting rod 30 to move the end portion 31 of the rod 28 along the slot 32, imparting a vibratory motion to the rod 28. The movement of the rod 28 vibrates the door 26 and thereby agitates the powder 24 at the bottom of the bin 22. The agitation of the door 26 and the contacting powder causes the release of the powder 24 as generally indicated by 29 into the air stream 21, as best shown in FIG. 3. The bin 22 is advantageously disposed above the airflow 21 such that the powder 24 when released falls by gravity into the airflow 21. The powder 24 is then carried by the airflow 21, impinging against the surface 45 of the test board 44. Some of the powder carried by the airflow 21 will adhere to the surface 45, the adhering amount being dependent on the degree of tackiness of the surface.

The powder laden airflow 21 is advantageously recirculated through the duct 20. The fan 14 and the motor 40 are operated for a specified time.

The board 44 is weighed before being placed in the chamber 2 and is reweighed after it has been subjected to the powder laden airflow 21. An indication of the degree of tackiness of the board 44 is provided by the percentage weight amount of the powder 24 that adheres to the board. The greater the percent weight of the powder sticking to the board, the greater the degree of tackiness of the board relative to another board with a lesser amount of adhering powder.

A person of ordinary skill in the art will appreciate that the tackiness tester A provides a reproducible and consistent method for gauging the degree of tackiness of the board 44. The tackiness tester A provides a standardized means for monitoring the degree of tackiness of a number of circuit boards after they are coated with flux in a flux deposit process. Appropriate adjustment to the process may be made based on the results provided by the tackiness tester A.

The powder 24 is preferably calcium carbonate, which is considered non-toxic. The particle size of the powder is preferably approximately 90 microns (170 mesh). The size of the particles is advantageously not too fine so that they would stick to almost any surface and are not too large and heavy so that they would not stick to the surface at all.

While this invention has been described as having preferred design, it is understood that it is capable of further modification, uses and/or adaptations of the invention following in general the principle of the invention and including such departures from the present disclosure as come within known or customary practice in the art to which the invention pertains and as may be applied to the essential features set forth and fall within the scope of the invention or the limits of the appended claims.

We claim:

1. A method for providing a measure of tackiness of a body surface, comprising the steps of:
   a) weighing the body;
   b) directing an airflow toward the body surface;
   c) dispensing powder into the airflow upstream of the surface such that the powder is carried by the airflow and impinges against the surface;
   d) maintaining the airflow for a period;
   e) permitting the powder to adhere to the surface; and
   f) weighing the body after the period, whereby an increase in weight of the body due to the adhering powder is a measure of tackiness of the surface.

2. A method as in claim 1, wherein:
   a) said step of directing an airflow includes the step of positioning the body within a closed chamber having inlet and outlet openings.

3. A method as in claim 1, wherein:
   a) said step of directing an airflow includes the step of directing the airflow substantially transversely to the surface.

4. A method as in claim 1, wherein:
   a) said powder is $CaCO_3$ powder.

5. A method as in claim 1, wherein:
   a) said step of dispensing powder includes the step of positioning the powder above the airflow.

6. A method as in claim 2, and including the step of:
   a) recirculating the airflow from the outlet opening into the inlet opening.

7. A method as in claim 2, and including the steps of:
   a) providing a storage for the powder, the storage having a bottom pivotable door disposed within the chamber and above the airflow; and
   b) periodically pivoting the door such that the powder is released into the airflow.

8. A method as in claim 4, and including the step of:
   a) selecting the powder particle size to be approximately 90 microns.

* * * * *